US007833983B2

(12) United States Patent
Mahler

(10) Patent No.: US 7,833,983 B2
(45) Date of Patent: Nov. 16, 2010

(54) ANALYTICAL METHOD AND KIT THEREOF

(75) Inventor: Michael Mahler, Neuss (DE)

(73) Assignee: Phadia, AB, Uppsala (SE)

( * ) Notice: Subject to any disclaimer, the term of this patent is extended or adjusted under 35 U.S.C. 154(b) by 1192 days.

(21) Appl. No.: 10/551,636

(22) PCT Filed: Apr. 2, 2004

(86) PCT No.: PCT/SE2004/000526

§ 371 (c)(1),
(2), (4) Date: Jun. 12, 2006

(87) PCT Pub. No.: WO2004/087745

PCT Pub. Date: Oct. 14, 2004

(65) Prior Publication Data

US 2006/0240477 A1  Oct. 26, 2006

(30) Foreign Application Priority Data

Apr. 2, 2003 (SE) .................................. 0300958

(51) Int. Cl.
*A61K 38/10* (2006.01)
*G01N 33/53* (2006.01)
(52) U.S. Cl. .......................................... 514/14; 435/7.1
(58) Field of Classification Search ........................ None
See application file for complete search history.

(56) References Cited

U.S. PATENT DOCUMENTS

2002/0165355 A1* 11/2002 Meheus et al. ............... 530/350

OTHER PUBLICATIONS

Abuaf, N., Johanet, C, Chretien, P, Absalon, B. 1., Homberg, J. C., Buri, J. F. , "Detection of autoantibodies to Sm antigen in systemic lupus erythematosus by immunodiffusion, ELISA and immunoblotting: variability of incidence related to assays and ethnic origin of patients", *European Journal of Clinical Investigation* 1990 20(4) pp. 354-359.
Arbuckle, M. R., Reichlin, M, Harley, J. B, James, J. A., "Shared early autoantibody recognition events in the development of anti-Sm B/B in human lupus", *Scandinavian Journal of Immunology*, 1999 50(5) pp. 447-455.
Arnett, F. C.,Edworthy, S. M., Bloch, D. A., McShane, D. J., Fries, J. F, Cooper, N. S., Healey, L. A, Kaplan, S. R, Liang, M. H, Luthra, H. S., "The American Rheumatism Association 1987 revised criteria for the classification of rheumatoid arthritis", *Arthritis & Rheumatism*, 1988 3 1(3) pp. 315-324.
Arnett, F. C., Hamilton, R. G, Roebber, M. G, Harley, J. B, Reichlin, M., "Increased frequencies of Sm and nRNP autoantibodies in American blacks compared to whites with systemic lupus erythematosus", *Journal of Rheumatology*, 1988 15(12) pp. 1773-1776.
Bloom, D. D, Davignon, J. L, Cohen, P. L, Elsenberg, R. A, Clarke, S. H., "Overlap of the anti-Sm and anti-DNA responses of MRL/Mp-lpr/lpr mice", *Journal of Immunology*, 1993 150(4) pp. 1579-1590.

Brahms, H, Raker, V. A, van Venrooij, W. J, Luhrmann, R., "A major, novel systemic lupus erythematosus autoantibody class recognizes the E, F, and G Sm snRNP proteins as an E-F-G complex but not in their denatured states", *Arthritis & Rheumatism*, 1997 40(4) pp. 672-682.
Brahms, H, Raymackers, J, Union, A, de Keyser, F, Meheus, L, Luhrmann, R., "The C-terminal RG dipeptide repeats of the spliceosomal Sm proteins D1 and D3 contain symmetrical dimethylarginines, which form a major B-cell epitope for anti-Sm autoantibodies", *J Biol Chem*, 2000 275(22) pp. 17122-17129.
Brahms, H, Meheus, L, De Brabandere, V, Fischer, U, Luhrmann, R., "Symmetrical dimethylation of arginine residues in spliceosomal Sm protein B/B and the Sm-like protein LSm4, and their interaction with the SMN protein", *Rna-A Publication of the Rna Society*, 2001 7 (11) pp. 1531-1542.
Sabbatini, A, Bombardieri, S, Migliorini, P., "Autoantibodies from patients with systemic lupus erythematosus bind a shared sequence of SmD and EpsteinBarr virus-encoded nuclear antigen EBNA 1", *European Journal of Immunology*, 1993 23(5) pp. 1146-1152.
Sabbatini, A, Doicher, M. P, Marchini, B, Bombardieri, S, Migliorini, P., "Mapping of epitopes on the SniD molecule: the use of multiple antigen peptides to measure autoantibodies in systemic lupus erythematosus", *Journal of Rheumatology*, 1993 20(10) pp. 1679-1683.
Seraphin, B., "Sm and Sm-like proteins belong to a large family: identification of proteins of the U6 as well as the U1, U2, U4 and U5 snRNPs", *Embo J*, May 1, 1995 14(9) pp. 2089-2098.
Tan, E. M, Kunkel, H. G., "Characteristics of a soluble nuclear antigen precipitating with sera of patients with systemic lupus erythematosus", *Journal of Immunology*, 1966 96(3) pp. 464-471.
Tan, E. M, Cohen, A. S, Fries, J. F, Masi, A. T, McShane, D. J, Rothfield, N. F, Schaller, J. G, Talal, N, Winchester, R. J, "The 1982 revised criteria for the classification of systemic lupus erythematosus", *Arthritis &Rheumatism*, 1982 25(11) pp. 1271-1277.
von Muhlen, C. A, Tan, E. M., "Autoantibodies in the diagnosis of systemic rheumatic diseases", *Seminars in Arthritis & Rheumatism*, 1995 24(5) pp. 323-358.
Ou, Y, Sun, D, Sharp, G. C, Hoch, S. O, "Screening of SLE sera using purified recombinant Sm-D1 protein from a baculovirus expression system", *Clinical Immunology & Immunopathology*, 1997 83 (3) pp. 310-317.
Zhang, W., Reichlin, M., "IgM anti-A and D SnRNP proteins and IgM anti-dsDNA are closely associated in SLE sera", *Clinical Immunology & Immunopathology*, 1995 74(1) pp. 70-76.

(Continued)

*Primary Examiner*—Christina Bradley
(74) *Attorney, Agent, or Firm*—Porter, Wright, Morris & Arthur LLP

(57) ABSTRACT

The present invention relates to a peptide comprising a symmetrical dimethylated arginine, and constitute an immunologic determinant of antibodies present in sera from patients with systemic lupus erythematosus (SLE), and wherein the methylation is a prerequisite for reacting with said antibodies. The invention also relates to the use of said peptide for diagnosis of SLE and the differentiation between SLE and MCTD.

11 Claims, 7 Drawing Sheets

OTHER PUBLICATIONS

Anonymous, "Preliminary criteria for the classification of systemic scierosis (scieroderma). Subcommittee for scieroderma criteria of the American Rheumatism Association Diagnostic and Therapeutic Criteria Committee", *Arthritis & Rheumatism*, 1980 23(5) pp. 581-590.

Mahler, M, Mierau, R, Schiumberger, W, Bluthner, M., "A population of autoantibodies against a centromere-associated protein A major epitope motif cross-reacts with related cryptic epitopes on other nuclear autoantigens and on the Epstein-Barr nuclear antigen 1", *Journal of Molecular Medicine*, 2001 79(12) pp. 722-731.

Marchini, B, Doicher, M. P, Sabbatini, A, Klein, G, Migliorini, P., "Immune response to different sequences of the EBNA 1 molecule in Epstein-Barr virus-related disorders and in autoimmune diseases", *Journal of Autoimmunity*, 1994 7(2) pp. 179-191.

McClain, M. T, Ramsiand, P. A, Kaufman, K. M, James, J. A., "Anti-sm autoantibodies in systemic lupus target highly basic surface structures of complexed spliceosomal autoantigens", *Journal of Immunology*, 2002 168(4) pp. 2054-2062.

Panush, R. S, Edwards, N. L, Longley, S, Webster, E., "'Rhupus' syndrome", *Archives of Internal Medicine*, 1988 148(7) pp. 1633-1636.

Reichlin, M, Martin, A, Taylor-Albert, E, Tsuzaka, K., Zhang, W., Reichlin, M. W., Koren, E., Ebling, F. M., Tsao, B., Hahn, B. II, "Lupus autoantibodies to native DNA cross-react with the A and D SnRNP polypeptides", *J Clin Invest*, Jan. 1994 93(1) pp. 443-449.

Riemekasten, G, Marell, J, Trebeljahr, G, Klein, R, Hausdorf, G, Haupi, T., Schneider-Mergener, J., Burmester, G. R., Hiepe, F., "A novel epitope on the C-terminus of SmD1 is recognized by the majority of sera from patients with systemic lupus erythematosus", *J Clin Invest*, Aug. 15, 1998 102(4) pp. 754-763.

Riemekasten, G., Kawald, A., Weiss, C., Meine, A., Marell, J., Klein, R., Hocher, B., Meisel, C., Hausdorf, G., Manz, R., Kamradt, T., Burmester, G. R., Hiepe, F., "Strong acceleration of murine lupus by injection of the SmD1(83-1 19) peptide", *Arthritis & Rheumatism*, 2001 44(10) pp. 2435-2445.

Rokeach, L. A., Haselby, J. A., Hoch, S. O., "Molecular cloning of a cDNA encoding the human Sm-D autoantigen", *Proc Natl Acad Sci U S A*, Jul. 1988 85(13) pp. 4832-4836.

Rokeach, L. A., Jannatipour, M, Haselby, J. A. Hoch, S. O., "Mapping of the immunoreactive domains of a small nuclear ribonucleoprotein-associated Sm-D autoantigen", *Clinical Immunology & Immunopathology*, 1992 65(3) pp. 315-324.

Rokeach, L. A., Hoch, S. O., "B-cell epitopes of Sm autoantigens", *Molecular Biology Reports*, 1992 16(3) pp. 165-174.

De Keyser, F., Hoch, S. O., Takei, M., Dang, H., De Keyser, II., Rokeach, L. A., Talal, N, "Cross-reactivity of the B/B' subunit of the Sm ribonucleoprotein autoantigen with proline-rich polypeptides", *Clinical Immunology & Immunopathology*, 1992 62(3) pp. 285-290.

Gausepohl, fl., Behn, C., Automated synthesis of solid—Phase bound peptides. In "Peptides arrays on membrane supports, synthesis and applications", *J Koch and M. Mahler, Eds*, pp. 55-68, Springer Verlag, Heidelberg, New York, 2002.

Greidinger, E. L., Hoffman, R. W., "The appearance of U1 RNP antibody specificities in sequential autoimmune human antisera follows a characteristic order that implicates the U1-70 kd and B'fB proteins as predominant U1 RNP immunogens", *Arthritis & Rheumatism*, 2001 44(2) pp. 368-375.

Hirakata, M., Craft, J., Hardin, J. A., "Autoantigenic epitopes of the B and D polypeptides of the U 1 snRNP. Analysis of domains recognized by the Y12 monoclonal anti-Sm antibody and by patient sera", *Journal of Immunology*, 1993 150 (8ptl) pp. 3592-3601.

Hoch, S. O., Eisenberg, R. A., Sharp, G. C., "Diverse antibody recognition patterns of the multiple Sm-D antigen polypeptides", *Clinical Immunology*, 1999 92(2) pp. 203-208.

Hoch, S. O., The Sm antigens. In "Manual of biological markers of disease", *R.N. Maini and W. J. van Venrooji, Eds*, pp. B2.4/1-29, Kluwer Academic, Dordrecht, The Netherlands, 1994.

Jaekel, H. P., Klopsch, T., Benkenstein, B., Grobe, N., Baldauf, A., Schoessler, W., Werle, E., "Reactivities to the Sm autoantigenic complex and the synthetic SmD1-aa83-119 peptide in systemic lupus erythematosus and other autoimmune diseases.", *Journal of Autoimmunity*, 2001 17(4) pp. 347-354.

James, J. A., Kaufman, K. M., Farris, A. D., Taylor-Albert, E.; Lehman, T. J., Harley, J. B., "An increased prevalence of Epstein-Barr virus infection in young patients suggests a possible etiology for systemic lupus erythematosus", *J Clin Invest*, Dec. 15, 1997 100(12) pp. 3019-3026.

Lehmeier, T., Raker, V., Hermann, H., Luhrmann, R., "cDNA cloning of the Sm proteins D2 and D3 from human small nuclear ribonucleoproteins: evidence for a direct D1-D2 interaction", *Proc Nati Acad Sci U S A*, Dec. 6, 1994 9 1(25) pp. 12317-12321.

Lerner, M. R., Boyle, J. A., Mount, S. M., Wolin, S. L., Steitz, J. A., "Are snRNPs involved in splicing?", *Nature*, 1980 283 (5743) pp. 220-224.

Gary et al, "The Predominant Protein-arginine Methyltransferase from *Saccharomyces cerevisiae*", *The Journal of Biological Chemistry*, vol. 271, No. 21, Issue of May 24, 1996, pp. 12585-12594.

* cited by examiner

R = arginine
S = symmetrical dimethylarginine
A = asymmetrical dimethylarginine

R = arginine
S = symmetrical dimethylarginine
A = asymmetrical dimethylarginine

Fig.
1. c.)
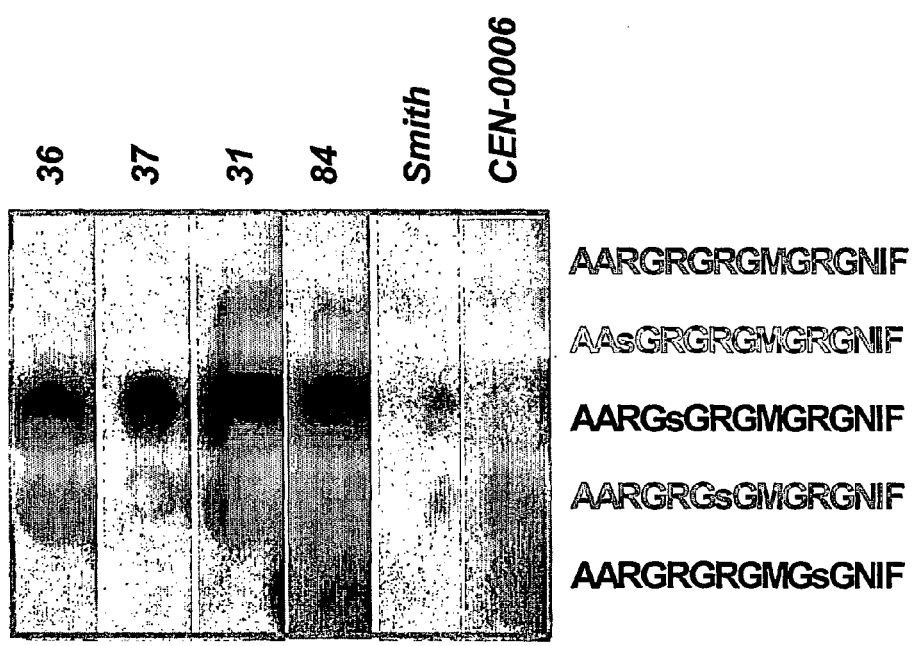

Fig. 2a

|  | Antibody concentration | | |
|---|---|---|---|
|  | Low | Medium | High |
| Intra-assay | | | |
| Mean [U/ml] | 7.1 | 36.3 | 83.8 |
| CV (%) | 1.82 | 3.79 | 6.52 |
| Inter-assay | | | |
| Mean [U/ml] | 7.48 | 36.54 | 91 |
| CV (%) | 3.97 | 7.42 | 2.27 |

```
                             SEQUENCE LISTING

<160> NUMBER OF SEQ ID NOS: 26

<210> SEQ ID NO 1
<211> LENGTH: 15
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (5)..(5)
<223> OTHER INFORMATION: METHYLATION, symmetric

<400> SEQUENCE: 1

Ala Ala Arg Gly Arg Gly Arg Gly Met Gly Arg Gly Asn Ile Phe
1               5                   10                  15

<210> SEQ ID NO 2
<211> LENGTH: 8
<212> TYPE: PRT
<213> ORGANISM: Homo sapiens

<400> SEQUENCE: 2

Pro Pro Pro Gly Met Arg Pro Pro
1               5

<210> SEQ ID NO 3
<211> LENGTH: 15
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (3)..(3)
<223> OTHER INFORMATION: METHYLATION, symmetric
<220> FEATURE:
<221> NAME/KEY: MOD_RES
<222> LOCATION: (5)..(5)
<223> OTHER INFORMATION: METHYLATION, symmetric
<220> FEATURE:
<221> NAME/KEY: MOD_RES
<222> LOCATION: (7)..(7)
<223> OTHER INFORMATION: METHYLATION,, symmetric
<220> FEATURE:
<221> NAME/KEY: MOD_RES
<222> LOCATION: (11)..(11)
<223> OTHER INFORMATION: METHYLATION, symmetric

<400> SEQUENCE: 3

Ala Ala Arg Gly Arg Gly Arg Gly Met Gly Arg Gly Asn Ile Phe
1               5                   10                  15

<210> SEQ ID NO 4
<211> LENGTH: 15
<212> TYPE: PRT
```

```
<213> ORGANISM: Artificial
<220> FEATURE:
<223> OTHER INFORMATION: Synthesized peptide

<400> SEQUENCE: 4

Ala Ala Arg Gly Arg Gly Arg Gly Met Gly Arg Gly Asn Ile Phe
1               5                   10                  15

<210> SEQ ID NO 5
<211> LENGTH: 9
<212> TYPE: PRT
<213> ORGANISM: Homo sapiens

<400> SEQUENCE: 5

Arg Gly Arg Gly Arg Gly Met Gly Arg
1               5

<210> SEQ ID NO 6
<211> LENGTH: 15
<212> TYPE: PRT
<213> ORGANISM: Artificial
<220> FEATURE:
<223> OTHER INFORMATION: Synthesized peptide

<400> SEQUENCE: 6

Asp Val Glu Pro Lys Val Lys Ser Lys Lys Arg Glu Ala Val Ala
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthesized peptide

<400> SEQUENCE: 7

Val Glu Pro Lys Val Lys Ser Lys Lys Arg Glu Ala Val Ala Gly
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthesized peptide

<400> SEQUENCE: 8

Pro Lys Val Lys Ser Lys Lys Arg Glu Ala Val Ala Gly Arg Gly
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthesized peptide

<400> SEQUENCE: 9

Val Lys Ser Lys Lys Arg Glu Ala Val Ala Gly Arg Gly Arg Gly
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthesized peptide
```

```
<400> SEQUENCE: 10

Ser Lys Lys Arg Glu Ala Val Ala Gly Arg Gly Arg Gly Arg Gly
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthesized peptide

<400> SEQUENCE: 11

Lys Arg Glu Ala Val Ala Gly Arg Gly Arg Gly Arg Gly Arg Gly
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthesized peptide

<400> SEQUENCE: 12

Glu Ala Val Ala Gly Arg Gly Arg Gly Arg Gly Arg Gly Arg Gly
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthesized peptide

<400> SEQUENCE: 13

Val Ala Gly Arg Gly Arg Gly Arg Gly Arg Gly Arg Gly Arg Gly
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthesized peptide

<400> SEQUENCE: 14

Gly Arg Gly Arg Gly Arg Gly Arg Gly Arg Gly Arg Gly Arg Gly
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthesized peptide

<400> SEQUENCE: 15

Gly Arg Gly Arg Gly Arg Gly Arg Gly Arg Gly Arg Gly Gly Pro
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthesized peptide
```

```
<400> SEQUENCE: 16

Gly Arg Gly Arg Gly Arg Gly Arg Gly Arg Gly Gly Pro Arg Arg
1               5                   10                  15

<210> SEQ ID NO 17
<211> LENGTH: 15
<212> TYPE: PRT
<213> ORGANISM: Artificial
<220> FEATURE:
<223> OTHER INFORMATION: Synthesized peptide

<400> SEQUENCE: 17

Gln Val Ala Ala Arg Gly Arg Gly Arg Gly Met Gly Arg Gly Asn
1               5                   10                  15

<210> SEQ ID NO 18
<211> LENGTH: 15
<212> TYPE: PRT
<213> ORGANISM: Artificial
<220> FEATURE:
<223> OTHER INFORMATION: Synthesized peptide

<400> SEQUENCE: 18

Val Ala Ala Arg Gly Arg Gly Arg Gly Met Gly Arg Gly Asn Ile
1               5                   10                  15

<210> SEQ ID NO 19
<211> LENGTH: 15
<212> TYPE: PRT
<213> ORGANISM: Artificial
<220> FEATURE:
<223> OTHER INFORMATION: Synthesized peptide

<400> SEQUENCE: 19

Ala Ala Arg Gly Arg Gly Arg Gly Met Gly Arg Gly Asn Ile Phe
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthesized peptide

<400> SEQUENCE: 20

Ala Arg Gly Arg Gly Arg Gly Met Gly Arg Gly Asn Ile Phe Gln
1               5                   10                  15

<210> SEQ ID NO 21
<211> LENGTH: 15
<212> TYPE: PRT
<213> ORGANISM: Artificial
<220> FEATURE:
<223> OTHER INFORMATION: Synthesized peptide

<400> SEQUENCE: 21

Arg Gly Arg Gly Arg Gly Met Gly Arg Gly Asn Ile Phe Gln Lys
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthesized peptide

<400> SEQUENCE: 22
```

```
Gly Arg Gly Arg Gly Met Gly Arg Gly Asn Ile Phe Gln Lys Arg
1               5                   10                  15

<210> SEQ ID NO 23
<211> LENGTH: 15
<212> TYPE: PRT
<213> ORGANISM: Artificial
<220> FEATURE:
<223> OTHER INFORMATION: Synthesized peptide

<400> SEQUENCE: 23

Arg Gly Arg Gly Met Gly Arg Gly Asn Ile Phe Gln Lys Arg Arg
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (3)..(3)
<223> OTHER INFORMATION: METHYLATION, symmetric

<400> SEQUENCE: 24

Ala Ala Arg Gly Arg Gly Arg Gly Met Gly Arg Gly Asn Ile Phe
1               5                   10                  15

<210> SEQ ID NO 25
<211> LENGTH: 15
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (7)..(7)
<223> OTHER INFORMATION: METHYLATION, symmetric

<400> SEQUENCE: 25

Ala Ala Arg Gly Arg Gly Arg Gly Met Gly Arg Gly Asn Ile Phe
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (11)..(11)
<223> OTHER INFORMATION: METHYLATION, symmetric

<400> SEQUENCE: 26

Ala Ala Arg Gly Arg Gly Arg Gly Met Gly Arg Gly Asn Ile Phe
1               5                   10                  15
```

ANALYTICAL METHOD AND KIT THEREOF

RELATED APPLICATION

The present application is a 371 of PCT/SE2004/000526 filed Apr. 2, 2004.

FIELD OF THE INVENTION

The present invention relates to a peptide comprising a symmetrical dimethylated arginine, and constitute an immunologic determinant of antibodies present in sera from patients with systemic lupus erythematosus (SLE), and wherein the methylation is a prerequisite for reacting with said antibodies. The invention also relates to the use of said peptide for diagnosis of SLE and the differentiation of SLE and mixed connective tissue disease (MCTD).

BACKGROUND OF THE INVENTION

Systemic rheumatic diseases are characterized by the occurrence of circulating autoantibodies to defined intracellular targets (reviewed in von Mühlen and Tan, 1995). Among the earliest of those autoantibodies to be identified were the anti-Sm, which are closely associated with systemic lupus erythrematosus (SLE) (Tan and Kunkel 1966). Thus, anti-Sm antibodies have been included as one of the American College of Rheumatology classification criteria for this disease (Tan et al., 1982). Apart from autoantibodies targeting the Sm-complex anti-DNA, anti-PCNA, anti-U1-RNP, anti-nucleosome, anti-histone, anti-Ro/SS-A, anti-La/SS-B, anti-ribosomal RNP and anti-phopholipid antibodies are frequently found in patients suffering from SLE (von Mühlen and Tan 1995).

In average anti-Sm reactivity is found in 5-30% of patients with SLE, although the specific frequency will vary depending on the detection system and the ethnicity of the SLE population (Abuaf et al., 1990; Jaekel et al., 2001). The Sm-antigen is part of the spliceosomal complex that catalyzes the splicing of nuclear pre-mRNA (Seraphin, 1995; Lerner et al., 1980). The complex itself comprises at least nine different polypeptides with molecular weights ranging from 9-29.5 kDa [B (B1, 28 kDa), B' (B2, 29 kDa), N (B3, 29.5 kDa), D1 (16 kDa), D2 (16.5 kDa), D3 (18 kDa), E (12 kDa), F (11 kDa) and G (9 kDa)] (Hoch, 1994). All of those core proteins can serve as targets of the anti-Sm immune response, most frequently the B and D polypeptides, which are therefore considered the major antigens (Hoch, 1994; Brahms et al., 1997; Ou et al., 1997). However, SmBB' and U1 specific RNPs which are frequently the target of autoantibodies in patients with MCTD share crossreactive epitopes, consequently SmD is regarded as the most specific Sm-antigen (van Venrooij et al., 1991; Hoch et al., 1999). Within the SmD family the SmD1/D3 pattern is at least four times more common than SmD1/D2/D3 recognition with a pronounced immunoreactivity to SmD1 (Hoch et al., 1999). In epitope-mapping studies, several linear and conformational epitopes have been mapped on the SmB- and D-proteins (Rokeach et al., 1992; Hirakata et al., 1993). On SmD1 and BB' the major reactivity was predominantly found in the C-terminal extensions (Rokeach et al., 1992; Hirakata et al., 1993; Rokeach and Hoch, 1992). The epitope PPPGMRPP (SEQ ID NO: 2) that occurs three times within the C-terminal extensions of SmBB' was shown to crossreact with other prolin rich structures of spliceosomal autoantigens such as the U1 specific antigens and of retroviral proteins such as p24 gag of HIV-1 (De Keyser et al., 1992). Follow-up studies and immunization experiments revealed that this motif is consistently the earliest detectable SmBB' epitope acting as starting point of epitope-spreading events within the BB' molecule and to the SmD-polypeptides (Arbuckle, 1999; Greidinger and Hoffman, 2001).

A recent study identified five linear epitopes on SmD2 and four on SmD3 distributed on the entire molecules (McClain et al., 2002). All of these epitopes share basic properties and are exposed on the surface of the protein rendering them antigenic (McClain et al., 2002).

One of the described B-cell epitopes on SmD3 (epitope 4; aa 104-126) displayed close homology to an antigenic region from the SmD1 protein finally leading to crossreactivity (McClain et al., 2002). For diagnostic purposes a synthetic peptide corresponding to the C-terminal extension of SmD1 was used to develop an ELISA system with diagnostic sensitivities and specificities ranging from 36-70% and from 91.7% and 97.2%, respectively (Riemekasten et al., 1998; Jaekel et al., 2001). Recently, it has been shown, that the polypeptides D1, D3 and BB' contain symmetrical dimethylarginine (referred to herein as sdR or sDMA) constituting a major autoepitope within the C-terminus of SmD1 (Brahms et al., 2000; Brahms et al., 2001). In one of these studies a synthetic peptide of SmD1 (aa 95-119) containing sDMA demonstrated significant increased immunoreactivity compared to the non-modified peptide reflecting a conflict to previous data (Riemekasten et al., 1998; Brahms et al., 2000).

In WO 99/11667 a method is described for producing peptides containing methylated arginines and that constitute immunogenic determinants of antibodies present in sera from patients with SLE or Epstein-Barr virus (EBV) and wherein the methylation is a prerequisite for reacting with said antibodies. However, these peptides are generally described and no connection between peptide sequence and ability to diagnose autoimmune disease has been disclosed.

SUMMARY OF THE INVENTION

We have now found that our claimed peptide comprising a symmetrical dimethylated arginine at a defined position is essential for the diagnosis of SLE, and it has surprisingly been shown that this peptide can be used in a highly specific and reliable diagnostic immunoassay for selection of SLE patients and for the differentiation between SLE and MCTD. Multimers of the peptide can also be used for the same purposes. A kit comprising the claimed peptide kan be used for diagnosis of SLE as well as for differentiation between SLE and MCTD. The advantage of the claimed invention is that it does not pick up false positive samples from the group of MCTD samples.

It is an object of the present invention to provide an analytical method for detection of anti-Sm antibodies.

The present inventor has surprisingly found that symmetrical dimethylation of a certain arginine residue within the SmD3 sequence is crucial for its antigenicity.

Therefore, in one aspect, the present invention provides a peptide (S33) containing 15-16 amino acids, comprising symmetrical dimethylated arginine (sDMA), that is able to react with antibodies and with said dimethylation being crucial for the reaction between said peptide and said antibodies and wherein said antibodies are present in sera from patients with systemic lupus erythematosus (SLE).

In a second aspect the S33 peptide comprises the amino acid sequence AARG sdR GRGMGRGNIF (SEQ ID NO: 1).

In a third aspect the symmetric dimethylated arginine has the position 112 in the polypeptide sequence of SmD3.

In a fourth aspect the S33 peptide comprises a symmetric dimethylated arginine with the structure

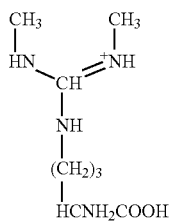

In a fifth aspect the invention is a method for use of the S33 peptide for in vitro diagnosis of SLE In a sixth aspect the invention is a method for use of the S33 peptide for differentiation of SLE and mixed connective tissue disease (MCTD).

In a seventh aspect the invention is a kit for use of the S33 peptide for in vitro monitoring of the disease activity in dsDNA negative SLE patients, wherein the disease activity is defined as a correlation between the antibody titer and to the new mimotope peptide and the disease activity.

In an eight aspect the invention is a method to follow the antibody titer by repeted testing in order to monitor the effect of treatment or the disease activity In a ninth aspect the invention is a multimer peptide comprising multiples of the S33 peptide

DETAILED DESCRIPTION OF THE INVENTION

EXAMPLE 1

Serum Samples

Figure 1A:
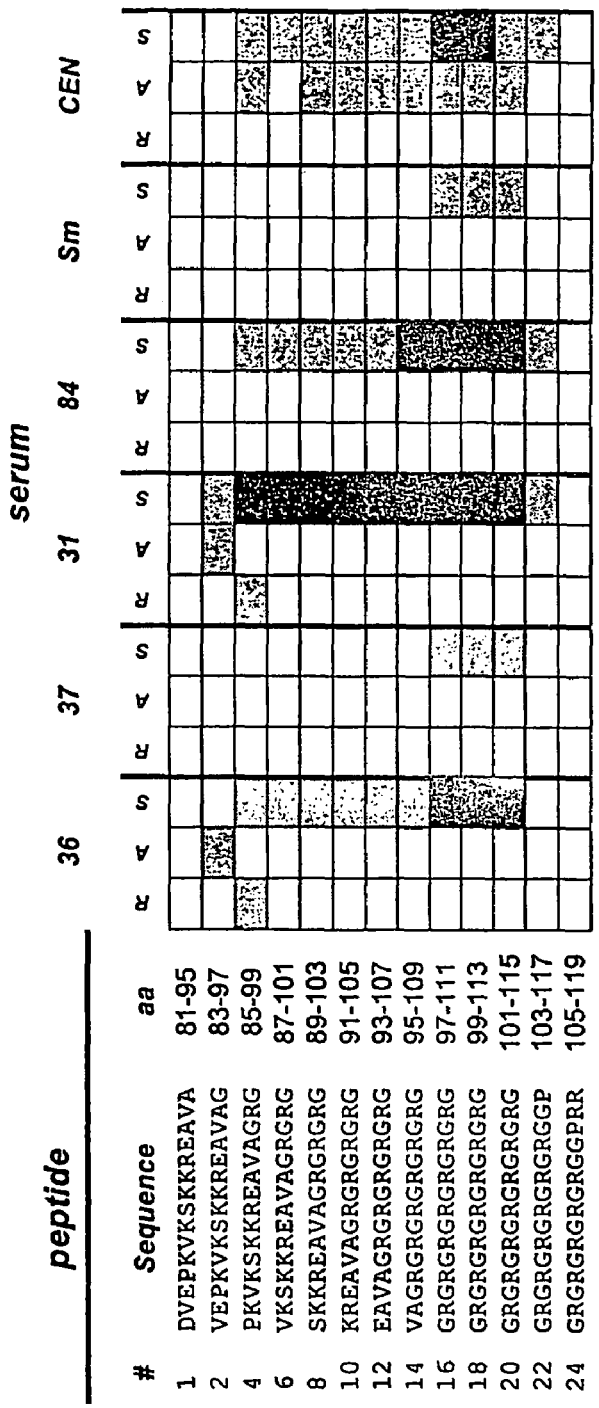
In FIG. 1a:
\# Sequence aa SEQ ID NO:
1 DVEPKVKSKKREAVA 81-95 (SEQ ID NO: 6)
2 VEPKVKSKKREAVAG 83-97 (SEQ ID NO: 7)
4 PKVKSKKREAVAGRG 85-99 (SEQ ID NO: 8)
6 VKSKKREAVAGRGRG 87-101 (SEQ ID NO: 9)
8 SKKREAVAGRGRGRG 89-103 (SEQ ID NO: 10)
10 KREAVAGRGRGRGRG 91-105 (SEQ ID NO: 11)
12 EAVAGRGRGRGRGRG 93-107 (SEQ ID NO: 12)
14 VAGRGRGRGRGRGRG 95-109 (SEQ ID NO: 13)
16 GRGRGRGRGRGRGRG 97-111 (SEQ ID NO: 14)
18 GRGRGRGRGRGRGRG 99-113 (SEQ ID NO: 14)
20 GRGRGRGRGRGRGRG 101-115 (SEQ ID NO: 14)
22 GRGRGRGRGRGRGGP 103-117 (SEQ ID NO: 15)
24 GRGRGRGRGRGGPRR 105-119 (SEQ ID NO: 16)
In FIG. 1b:
\# Sequence aa SEQ ID NO:
75 QVAARGRGRGMGRGN 106-120 (SEQ ID NO: 17)
76 VAARGRGRGMGRGNI 107-121 (SEQ ID NO: 18)
77 AARGRGRGMGRGNIF 108-122 (SEQ ID NO: 19)
78 ARGRGRGMGRGNIFQ 109-123 (SEQ ID NO: 20)
79 RGRGRGMGRGNIFQK 110-124 (SEQ ID NO: 21)
80 GRGRGMGRGNIFQKR 111-125 (SEQ ID NO: 22)
81 RGRGMGRGNIFQKRR 112-126 (SEQ ID NO: 23)
In FIG. 1c:
Sequence SEQ ID NO:
AARGRGRGMGRGNIF SEQ ID NO: 4
AAsGRGRGMGRGNIF SEQ ID NO: 24
AARGsGRGRGMGRGNIF SEQ ID NO: 1
AARGRGsGMGRGNIF SEQ ID NO: 25
AARGRGRGMGsGNIF SEQ ID NO: 26
wherein s =symmetrical dimethylarginine (sdR).

Sera (n=628) were collected from patients suffering from systemic lupus erytlhrematosus (SLE; n=176), rheumatoid arthritis (RA, n=86), Sjögren syndrome (SS, n=24); mixed connective tissue disease (MCTD, n=26), scleroderma (SSc, n=26) and polymyositis/dermatomyositis (PM/DM, n=13). All patients were classified according to the ACR-criteria for each disease (Tan et al., 1982; Arnett et al., 1988). To further assess the assay specificity, we analyzed a group of sera from patients with infection diseases (n=77) including hepatitis-C (HCV; n=30), cytomegalo (CMV; n=22) and Epstein-Barr Virus (EBV; n=25) as well as from 192 healthy blood donors. All sera were stored at −80° C. until use. For epitope-mapping a panel of five sera containing anti-Sm antibodies was used. As negative controls autoimmune sera with other antibody specificities than anti-Sm were selected.

Serological characterization of randomly selected SLE patient sera. All autoimmune patient sera were tested for autoantibodies to histones, dsDNA and the Sm-complex using quantitative Varelisa®s (Pharmacia Diagnostics, Freiburg, Germany). SLE sera and samples, which demonstrated unexpected results were also measured in the semi quantitative ANA-Split ELISA research Kit (Pharmacia, Freiburg, Germany). The latter assay contains the autoantigens U1-68 kDa, U1-A, U1-C, SMBB', SmD, Ro-52, Ro-60 and La. All ELISAs were performed according to the instructions of use.

EXAMPLE 2

Epitope-mapping with Immobilized Oligopeptides

The published sequences of SmD1, P13641, (Rokeach et al., 1988) and SmD3, P43331, (Lehmeier et al., 1994) were used to synthesize overlapping 15 mer peptides with a pipetting robot according to the protocol described by Gausepohl and Behn (2002). The C-terminal extensions of both polypeptides were synthesized with an offset of 2 amino acids (13 amino acids overlap). Each arginine containing peptide was synthesized as three variants, with natural arginine, with sDMA or with asymmetrical dimethylarginine (asDMA) at the respective positions. Later on, a highly reactive peptide of SmD3 was synthesized with certain combinations of natural arginine and sDMA. Following completion of the peptide synthesis non-specific binding sites were blocked by overnight incubation of the membranes in blocking buffer (BB) at room temperature (RT). After one washing step membranes were incubated with serum samples at a dilution of 1:100 in BB for 2 h at RT. Unbound antibodies were removed by three washing steps. For detection peroxidase conjugated goat-anti-human IgG antibody was diluted 1:5000 in BB and incubated for 75 min (RT). Superfluous secondary antibodies were removed by three washing steps. Finally, bound antibodies were visualized using the enhanced chemoluminiscence (ECL) detection-system. Assay conditions were used under which negative sera showed no reactivity.

EXAMPLE 3

S33-peptide ELISA

Preparation of ELISA-plates. The lyophilized S33 peptide was used to prepare a stock solution of 10 µg/µl, which was stored in aliquots at −20° C. until use. Binding of the peptide to ELISA plates was carried out using 2.5 µg/ml of the peptide in coating buffer in a final volume of 120 µl per well. The coating procedure was carried out at 15° C. for 20 h. Unspecific binding sites were blocked with blocking solution. After discarding the blocking solution solid phases were dried at 37° C. for 2 h and sealed.

The assay was performed according to the general protocol of the Varelisa® system (Pharmacia Diagnostics, Freiburg). Blood donors demonstrated a reactivity range of 0.4-11.5 U/ml resulting in a mean value of 2.2 U/ml and a SD of 1.2 U/ml. The cut-off was technically set to 13 U/ml after ROC-analysis. PPVs and NPVs were calculated at different cut-off values.

Precision and reproducibility. Measurements of imprecision (inter- and intra-assay variability) were performed with 4 and 6 replicates, respectively. To assess precision of the anti-S33 peptide ELISA suitable anti-Sm sera, a low value sample (L); a medium value sample (M) and a high value sample (H) were assayed in five independent runs on one day (inter-assay), or in a single run (intra-assay). For within-run precision L, M and H were measured in six replicates on one solid phase. The precision data was calculated using ANOVA analysis.

Linearity. The linearity was analyzed by testing dilutions (1:1; 2:3; 1:2; 1:4; 1:8; 1:16; 1:32) of the highest standard point (S6) and of the high value sample from the precision analysis (H). For each dilution point, a ratio of the measured reactivity to the expected value was calculated, and 1 was subtracted from this quotient.

EXAMPLE 4

Correlation Study

Randomly selected SLE sera (n=50) and various controls (n=100) were tested using the commercially available anti-Sm antibody tests from different suppliers (Sm test A—Sm Test D) and the results were compared to the findings of the anti-S33 ELISA test.

EXAMPLE 5

Follow-up Study of a SLE Patient

Figure 3:
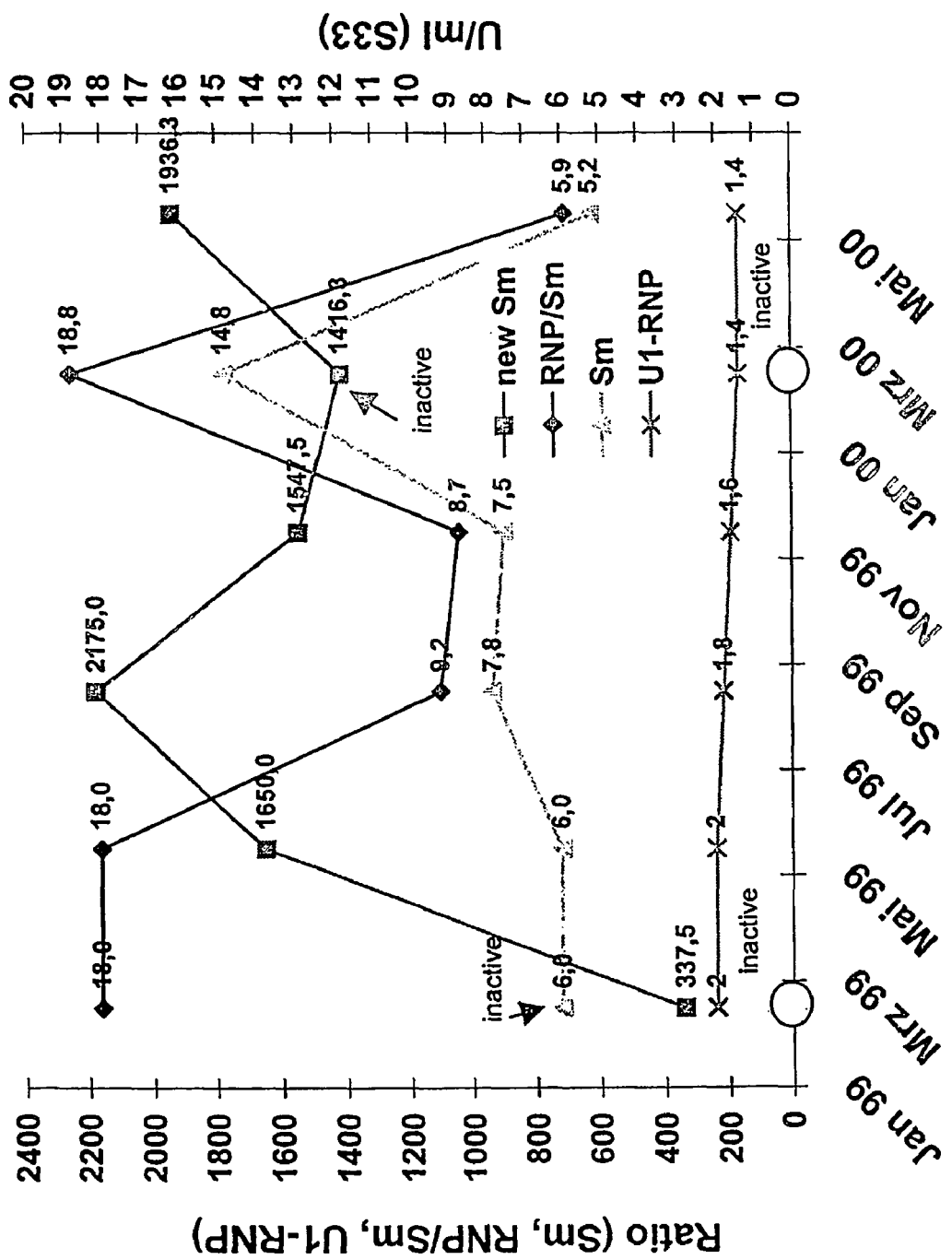
FIG. 3. A male SLE patient was clinically and serologically observed over a time period of 18 month.

A male SLE patient was clinically and serologically observed over a time period of 18 month (6 serum samples; see FIG. 3). The patient was tested for antibodies to the RNP/Sm complex, to the Sm antigen, to the isolated U1-RNP complex, to histones, to dsDNA and to the S33 peptide using the respective test kits from Pharmacia Diagnostics.

Results

Epitope fine-mapping of the C-terminal extensions of SmD1 and D3. To evaluate the effect of arginine-dimethylation on the antigenicity of SmD1 and SmD3 and to map relevant epitopes on both polypeptides a panel of anti-Sm sera was tested with peptide arrays (15 mer, 2 offset) covering the C-terminal region of SmD1 (P13641) and SmD3 (P43331).

Figure 1B:
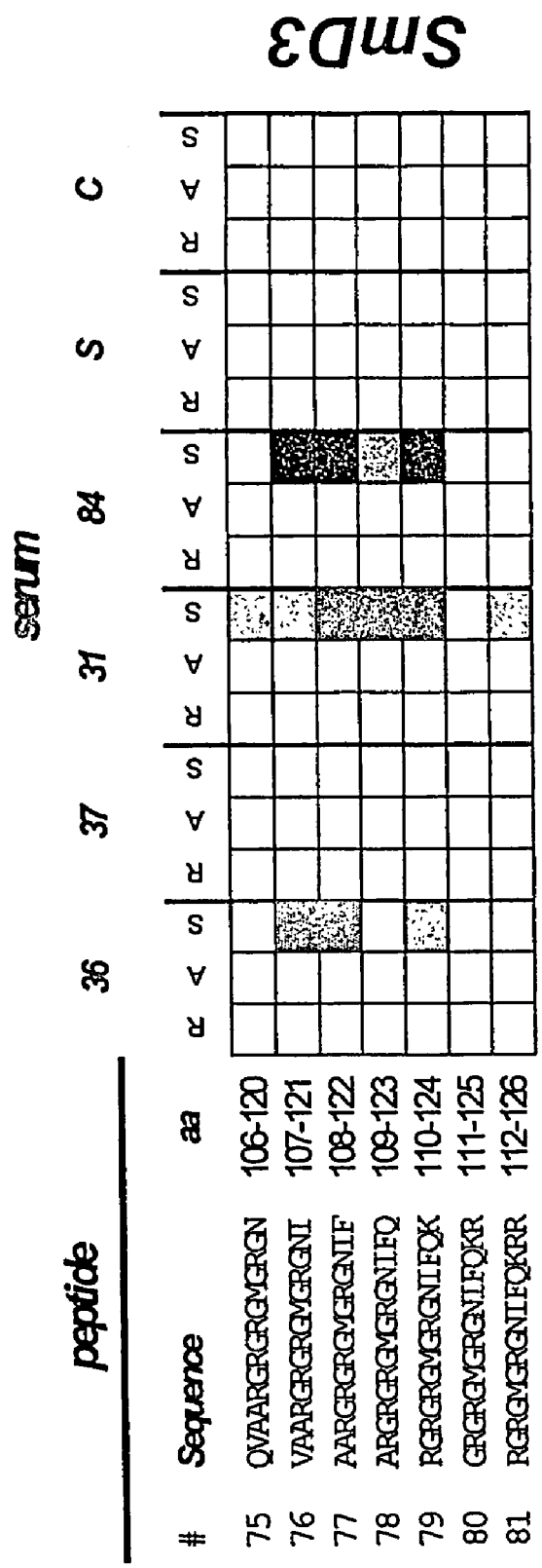
FIG. 1. Epitope analysis of SmD1 and SmD3. C-terminal extensions of SmD 1 (a) and SmD3 (b) were synthesized as peptide arrays (15 mers ; aa offset) and probed with patient sera. Immunoreactive peptide no. 77 was further tested as mimotope variants (c), wherein the following peptides are referenced.

The results show that dimethylation of arginine residues affects the binding of anti-Sm antibodies to C-terminal SmD1- and D3 polypeptides, significantly (see FIG. 1). All anti-SmD sera (#36, #37, #31, #84, #Sm) demonstrated an increased binding to SmD1 peptides containing the symmetrical form of dimethylarginine (sDMA). Especially the peptides that consist of glycine and DMA repeats, exclusively showed a strong reactivity with the antibodies (peptide no. 9, 10). Nevertheless, SmD1 polypeptides containing DMA represent a rather unspecific substrate for anti-Sm antibodies since they were also target of anti-centromere antibodies (ACA; #serum CEN (centromer)). Interestingly, those ACA bound also to peptides containing the asymmetrical form of DMA.

Binding experiments with peptides derived from SmD3 showed similar results. Only SmD3 peptides containing sDMA reacted with anti-Sm antibodies confirming the importance of the symmetric methylation of arginine residues (see FIG. 1b). In contrast to SmD1, no control serum (e.g. CEN) demonstrated antibody binding to SmD3 derived peptides reflecting a high specificity. One particular peptide (no. 77, $^{108}$AAsdRGsdRGsdRGMGsdRGNIF$^{122}$) (SEQ ID NO: 3) was strongly recognized by three out of five anti-Sm sera. Using a mutational analysis in which arginine residues of $^{108}$AARGRGRGMGRGNF$^{122}$ (SEQ ID NO: 4) were successively replaced by sDMA we were able to show that a mimotope peptide with a single dimethylated arginine residue at position 112 displayed immunoreactivity with all of the five anti-Sm sera (#36, #37, #31, #84, #Sm) but not with the controls (e.g. CEN; see FIG. 1c.). Thus, by introducing only one sDMA and at a defined position (amino acid 112) of SmD3, it was possible to increase the sensitivity of this peptide ($^{108}$AARGsdRGRGMGRGNIF$^{122}$; S33) (SEQ ID NO: 1) without a loss in specificity. This candidate peptide was subsequently synthesized as soluble antigen and used as substrate in ELISA.

Immunoserologic characterization of the SLE patient group. To evaluate if our SLE patient cohort represents a representative SLE serum panel approximately 100 SLE samples were randomly selected and tested for U1-68kD, U1-A, U1-C, SMBB', SmD, Ro-52/SS-A, Ro-60/SS-A, La/SS-B, histone dsDNA and β2-glycoprotein reactivity (Split ANA-Profil research assay, Pharmacia Diagnostics, Freiburg, Germany). The prevalence of the different autoantibodies was found in a good agreement to previous studies (Jaekel et al., 2001). Thus, with regard to their autoantibody profiles, the SLE cohort seems to be a representative SLE population. Results of the measurements of the SLE panel are summarized in table 1.

TABLE 1

Prevalence (%) of clinically relevant autoantibody
specificities in patients suffering from SLE (n = 101)
Autoantibodies to

| U1-68 | U1-A | U1-C | SmBB' | SmD | Ro-52 | Ro-60 | La | Histone | dsDNA | β2-Glycoprotein |
|---|---|---|---|---|---|---|---|---|---|---|
| 15.8 | 24.8 | 25.7 | 21.8 | 15.8 | 21.8 | 47.5 | 21.8 | 37.6 | 51 | 17 |

Anti-S33 Peptide ELISA

A 15 amino acid soluble peptide displaying highest sensitivity and specificity in the SPOT-assay ($^{108}$AARGsdRGRG-MGRGNIF$^{122}$) (SEQ ID NO: 1) was synthesized for technical reasons with an additional Cys at the C-terminus. This peptide was subsequently used to develop an ELISA system based on the general protocol of the Varelisa® tests (Pharmacia, Freiburg, Germany).

Figure 2B:
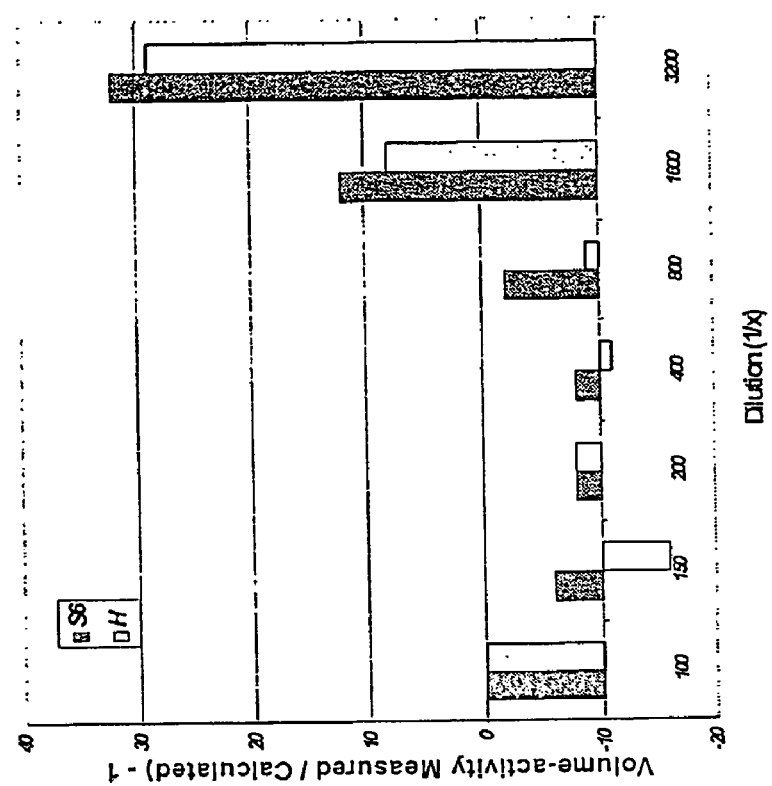
FIG. 2. Assay performance characteristics of the new anti-S33 assay. Intra- and interassay variability a.), linearity (b.), and Receiver Operating Characteristic ROC-analysis including Positive Predictive Value (PPV), Negative Predictive Value (NPV) and efficiency at different cut-offs (c.).
Figure 2B:
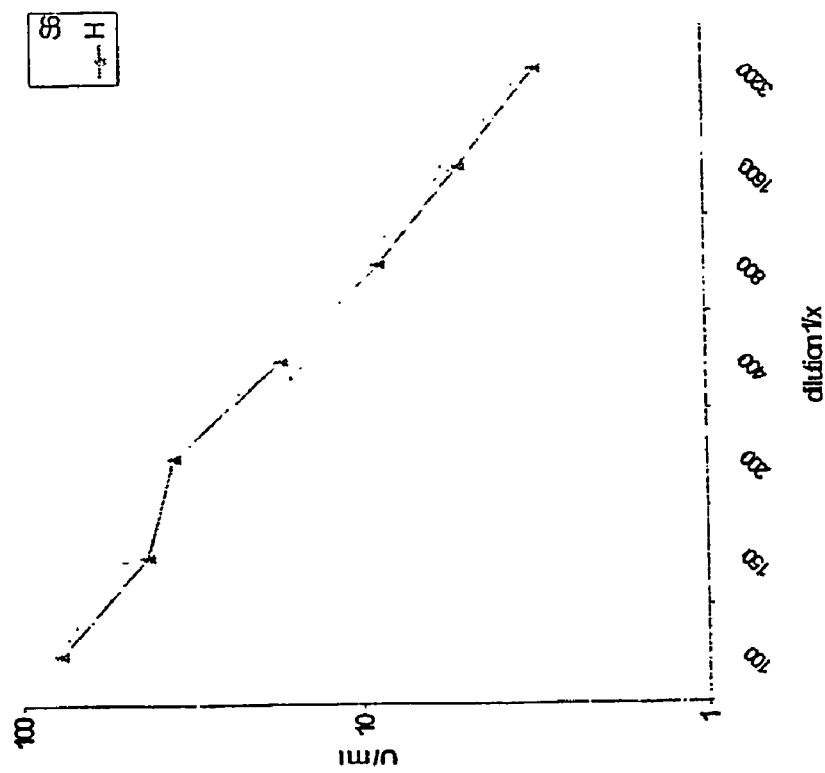
Figure 2C:
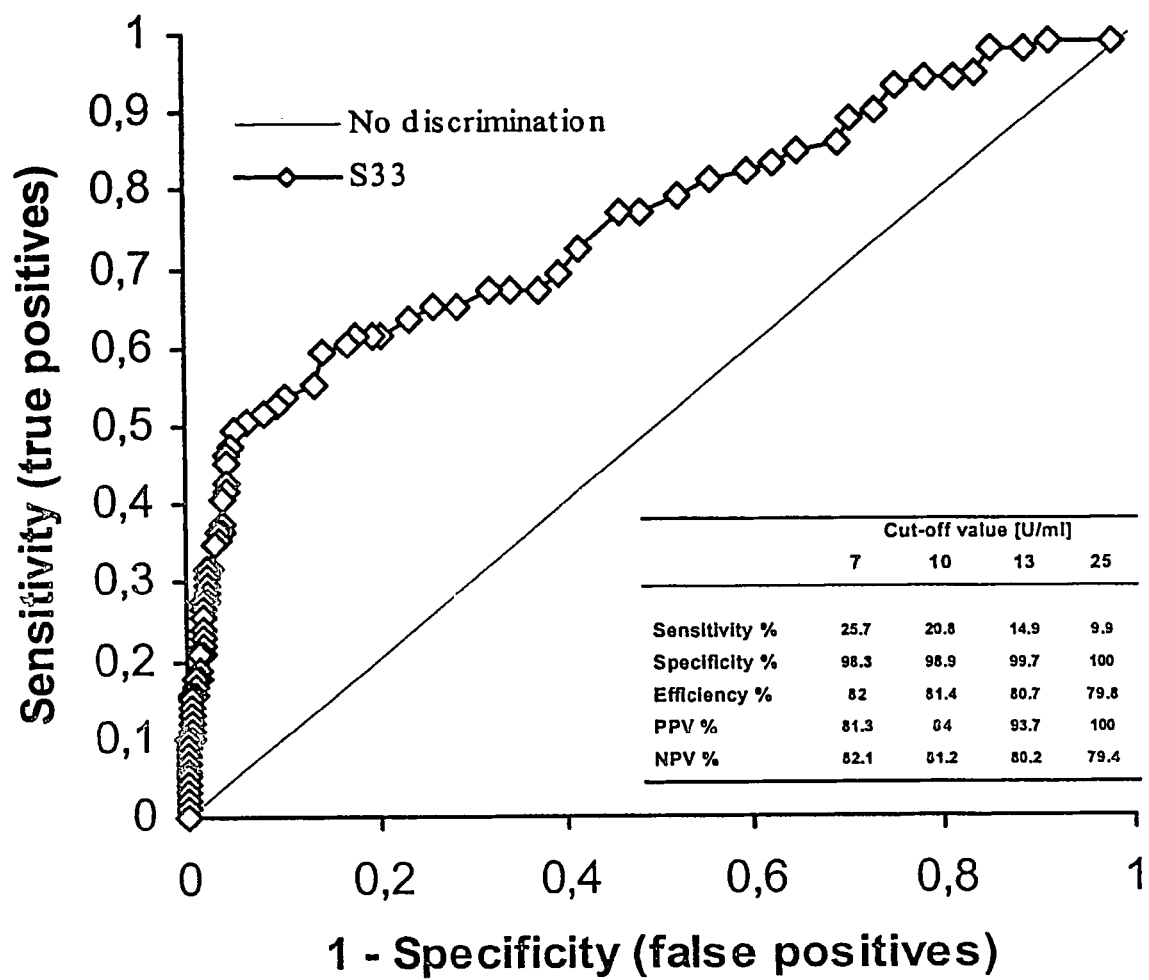

Assay performance characteristic. To evaluate the assay performance characteristics precision, reproducibility and linearity were analyzed. The intra- and interassay variability (CV %) of three samples were found ranging from 1.82 to 6.52% and from 2.27 to 7.42%, respectively. Dilution series of two samples demonstrated a linear range on five subsequent dilutions (>20% deviation). For the cut-off definition a receiver operating characteristic (ROC)-analysis was performed with SL1 and control sera. The assay performance characteristics of the new anti-S33-test including intra- and interassay variability (a.), linearity (b.), ROC-analysis, PPV, NPV and efficiency (c.) are summarized in FIG. 2 (a.-c.).

For the evaluation of the diagnostic relevance of the new test a technical cut-off of 13 U/ml was used to combine high specificity with moderate sensitivity. Sera from 176 SLE patients, from 181 autoimmune patients diagnosed differently than SLE, from 77 patients with infection diseases and from 192 human normal donors were analyzed in the new ELISA system. 28 SLE patients (15.9%) were tested positive for anti-S33 antibodies displaying a significantly increased reactivity of up to 952 U/ml with a mean value of 43 U/ml (SD=160.2 U/ml). Patients from related disorders demonstrated a significant reduced reactivity in the new ELISA system (mean 3.36 U/ml). Only one patient of the RA group was assayed positive (24.6 U/ml). None of the remaining controls including patients suffering from SSc (n=26), PM/DM (n=13), MCTD (n=126) or infection diseases (n=77) showed reactivity to the S33 peptide. The serum samples from patients with infectious diseases demonstrated a reduced reactivity (mean 0.67 U/ml; top value 3.3 U/ml), even when compared to the healthy donors (mean 2.21 U/ml; top value 11.5 U/ml). The top value of the infectious disease sera was found in the EBV group. Results are summarized in Table 2.

TABLE 2

Results of ELISA using S33 with SLE and various control sera

| | No. (%) of anti-S33-positve sera | Mean value (U/ml) | Top value (U/ml) |
|---|---|---|---|
| SLE (n = 176) | 28 (15.9) | 43.0 | 1190.0 |
| Rheumatic diseases (181) | 1 (0.6) | 2.2 | 24.6 |
| RA (86) | 1 (1.2) | 1.6 | 24.6 |
| pSS (24) | 0 | 1.9 | 3.9 |
| MCTD (26) | 0 | 3.1 | 12.8 |
| SSc (26) | 0 | 2.4 | 4.3 |
| PM/DM (13) | 0 | 2.8 | 9.6 |
| Infectious diseases (77) | 0 | 0.67 | 3.3 |
| HCV (30) | 0 | 0.42 | 1.1 |
| CMV (22) | 0 | 0.8 | 3.2 |
| EBV (25) | 0 | 0.78 | 3.3 |
| Healthy individuals (192) | 0 | 2.21 | 11.5 |

In summary, 15 samples of the SLE group (n=176) and only one serum of the controls (n=449, 0.2%) was tested positive resulting in a diagnostic specificity of 99.8% and a sensitivity of 15.9%. PPV and NPV, as well as the diagnostic efficiency was calculated at 96.6%, 75.3% and 76.3%, respectively (see FIG. 2c.). These data indicate that anti-S33 antibodies appear to be exclusively present in sera from SLE patients.

Apart from the anti-s33 peptide reactivity the false positive ra sample contains high titers of antibodies to the u1-rnps-68 kda (ratio 4.5), u1-c (ratio 9.4) and histones (133.8 u/ml) (see table 3). Anti-smbb' and anti-smd titers as determined by elisa were elevated when compared to the controls, but still below the cut-off values (see table 3).

TABLE 3

Autoantibody-profile of the false positive RA patient in the new S33 peptide assay

| Serum ID # | Control group | U1-68 kD* | U1-A* | U1-C* | SmBB'* | SmD* | Ro-52* | Ro-60* | La* | histone[1] [U/ml] | dsDNA[2] [U/ml] |
|---|---|---|---|---|---|---|---|---|---|---|---|
| R15 | Ra | 4.5 | 0.6 | 9.2 | 0.8 | 0.8 | 0.2 | 0.7 | 0.5 | 133.8 | 15.6 |

*semiquantitative Assay (ANA-Split); cut-off >1.4
[1]cut-off (30 U/ml)
[2]cut-off (55 U/ml)

Correlation to other autoantibodies. With regard to possible existing correlations between anti-S33 antibodies and other autoantibody species, a statistic evaluation was performed using the SLE panel of approximately 100 randomly selected sera. Significant correlations were to U1-68kDa (p=0.0335), U1-A (p<0.0001), U1-C (p<0.0001) SMBB' (p<0.0001), SmD (p<0.0001), dsDNA (p<0.0001) and histone (p<0.0001), but not to Ro-52 (p=0.2192), Ro-60 (p=0.2212) and La (p=0.8785) (see table 4).

Follow-up study of a SLE patient. A male SLE patient was clinically and serologically observed over a time period of 18 month (6 serum samples; see FIG. 3). At the beginning of the follow-up study the patient displayed a strong immunoresponse towards the RNP/Sm complex (ratio of 18), to the Sm antigen (ratio of 6), to the new Sm antigen (337.5 U/ml) and

TABLE 4

Association between anti-S33 positivity and other Aab species in SLE

| Aabto | U1-68 kD | U1-A | U1-C | SmBB' | SmD | Ro-52 | Ro-60 | La | histone | dsDNA | β2-Glycoprotein |
|---|---|---|---|---|---|---|---|---|---|---|---|
| S33+ | 8/16 | 12/25 | 11/26 | 11/22 | 11/16 | 5/22 | 12/48 | 4/22 | 10/38 | 13/51 | 4/16 |
|  | 50% | 48% | 42.3% | 50% | 68.8% | 22.7% | 25% | 18.2% | 26.3% | 25.5% | 25% |
| 2-tailed p | 0.0335* | <0.0001* | <0.0001* | <0.0001* | <0.0001* | 0.2192 | 0.2212 | 0.8785 | <0.0001* | <0.0001* | 0.3792 |

Pearson correlation;
*Statistically significant

Looking at the reactivity towards the Sm-complex, five samples of the randomly selected SLE patients (n=101) reacted with the purified SmD antigen, but not with the S33 peptide. The remaining 11 SmD positive sera (68.8%) were also tested positive in the new anti-S33 peptide ELISA. Interestingly, among the anti-S33 positive samples, 4 patients (#89, #92, #20627, #9811) were found, all anti-SmD negative showing anti-S33 peptide reactivities of 15.4, 21.3, 41.3 and 13.9 units, respectively.

To evaluate correlations to commercially available anti-Sm antibody tests from different suppliers 50 randomly selected SLE sera from the SLE patient group and 100 controls were tested using the anti-Sm antibody tests from different suppliers. 6 out of 50 SLE sera (12%) and none of the controls (0%) were positive in the anti-S33 antibody test resulting in a sensitivity of 12% and a specificity of 100%. In contrast the anti-Sm assay from different suppliers Sm test A, B and C accessed only 5 SLE samples (10%) and between 6 (Sm test A, C) and 12 (Sm test D) patients from the control group. The majority of false positive results were found within the group of MCTD patients (see Table 5).

a moderate response to the isolated U1-RNP complex (ratio of 2) as well as to histones (59.5 U/ml). No reactivity to dsDNA could be found (19.1 U/ml; cut-off 55 U/ml). At that time point the medical record reported an inactive phase of disease. Later on the antibody titer towards the new Sm antigen significantly increased reaching its peak in the third serum sample withdrawn in August 1999. In contrast a decreasing anti-RNP/Sm titer could be observed between the second and the fourth blood sampling followed by another strong increase in the fifths sample. At that time point the titer against the new Sm antigen (S33) was lower than before and the disease status was reported as inactive according to the medical record. No significant alterations could be observed in the anti-dsDNA and anti-histone titer during the observation time of the patient.

In the presented examples the anti-Sm immune response have been analyzed towards the Sm antigens D1 and D3, which are considered to be the SLE specific polypeptides (van Venrooji et al., 1991; Hoch et al., 1999). Using immobilized peptides it has been shown that symmetric dimethylation of arginine residues plays an important role in the formation of

TABLE 5

Reactivity of control sera, mainly MCTD in the tests from different suppliers

| Serum | | | Immunoassays | | | | |
|---|---|---|---|---|---|---|---|
| No. | ID | Diagnosis | Varelisa(R) ® S33 U/ml | Sm Test A RE | Sm Test B Units | Sm Test C Ratio | Sm Test D Ratio |
|  |  |  | 13[#] | 20[#] | 40[#] | 1[#] | 1[#] |
| 105 | 25516 | MCTD | 3.0 | 87.9 | 118.8 | 1.1 | 4.8 |
| 107 | 25518 | MCTD | 1.0 | 14.4 | 37.5 | 0.3 | 1.4 |
| 108 | 25519 | MCTD | 0.0 | 6.7 | 52.0 | 0.9 | 2.7 |
| 110 | 25521 | MCTD | 0.5 | 87.4 | 111.7 | 1.5 | 4.2 |
| 112 | 25523 | MCTD | 0.0 | 21.6 | 34.1 | 0.6 | 0.3 |
| 121 | 25532 | MCTD | 2.6 | 7.4 | 26.9 | 0.3 | 3.5 |
| 123 | 25534 | MCTD | 1.1 | 10.5 | 41.7 | 0.6 | 2.3 |
| 126 | 25537 | MCTD | 3.2 | 7.2 | 41.4 | 0.3 | 0.3 |
| 128 | 25539 | MCTD | 0.7 | 4.2 | 67.1 | 0.5 | 3.7 |
| 129 | 25540 | MCTD | 4.1 | 118.5 | 132.4 | 2.4 | 3.1 |
| 132 | 25543 | MCTD | 2.4 | 12.8 | 42.7 | 0.3 | 2.3 |
| 133 | 25544 | MCTD; SLE | 9.9 | 136.0 | 153.7 | 7.9 | 5.4 |
| 137 | 25448 | SSc | 2.2 | 72.2 | 105.3 | 1.2 | 2.8 |
| 145 | 25456 | MCTD | 1.1 | 8.4 | 30.9 | 0.3 | 1.5 |

[#]suggested cut-off values the major B-cell epitopes on both autoantigens. This observation was found in a good agreement to the result of Brahms et al. (2000) and thus contradictory to the findings of Riemekasten and colleagues (1998). Interestingly and in addition to previous investigations, it was found that with peptides as previously described the specificity of SmD3 peptides was higher than of those derived from SmD1.

McClain and colleagues (2002) described four antigenic regions on SmD3 of which antigenic region 4 covers the area 104-126. In this invention peptides synthesized on pins were subjected to analysis but without using the modified form of arginine. In the present invention reactivity within this region was only found in case natural arginine was replaced by sDMA. These contradictory results might be explained by the use of different sera, methology and/or by the varying peptide length. Three out of five sera specifically recognized the peptide $^{108}$AAsdRGsdRGsdRGMGsdRGNIF$^{122}$ (SEQ ID NO: 3) of this example.

Interestingly, the dimethylation of only one arginine and at a defined position (aa 112) could further increase the sensitivity of this particular mimotope peptide without a loss in specificity. Based on this data a candidate peptide was used ($^{108}$AARGsdRGRGMGRGNIF$^{122}$) (SEQ ID NO: 1) to develop an ELISA system. The new anti-Sm assay (anti-S33) demonstrated a sensitivity of 14.9% and a specificity of 99.7% for lupus resulting in a high positive (PPV; 93.7%) and negative predictive value (NPV; 80.2%) and thus a high diagnostic efficiency (80.7%). Therefore this test offers new opportunities for the diagnosis of systemic lupus erythrematosus, especially for the differentiation between SLE and MCTD as revealed by the correlation study.

Looking at the biochemical properties of the identified Sm-epitopes reveals that the pI can be regarded as predictor of antigenicity on the Sm-complex. On U1-RNP-A, SmB' and D1, the average pI of antigenic regions was 10.4 (nonantigenic 6.0) and on SmD2 and D3 more than pIs 9.0 (McClain et al., 2002). These inventive findings fit well to the high pI of the S33 peptide (>12.88). Whether the basic character simply increases the probability of surface exposure of these regions and thus the accessibility to antibodies has to be further investigated.

EBV, EBNA and anti-SmD antibodies. Epitope-mapping studies on SmD1 have identified an epitope-motif (aa 95-119) that cross-reacts with a homologue sequence 35-58 of the Epstein-Barr virus nuclear antigen 1 (EBNA-1) (Sabbatini et al., 1993; Sabbatini et al., 1993; Marchini et al., 1994). A more recent study has shown that this epitope also cross-reacts with a homologue region of SmD3 containing glycine arginine repeats (RGRGRGMGR) (SEQ ID NO: 5) (McClain et al., 2002). Moreover it became evident that GPRR (aa 114-119 on SmD1) represents a common cross-reactive autoepitope motif, which is present not only on EBNA-1, but also on a variety of autoantigens including CENP-A, B, C, SmBB', SmD1 and Ro-52, to term only a few (Mahler et al., 2001). Thus patients suffering from infectious mononucleosis or SLE related disorders might be tested false positive in ELISAs using the C-terminal extensions of SmD1 or SmD3. Furthermore, several studies have suggested an influence of EBV on the development of Lupus-like conditions (James et al., 1997). Therefore, it is considered that the use of EBV positive sera as controls is an important finding towards a highly specific and reliable anti-SmD immunoassay. Among the 25 EBV disease controls presented, no false positive sample was found confirming the suggested high specificity of the anti-S33-abs assay. Unfortunately, Riemekasten and colleagues (1998) did not include this patient group in the evaluation of their test.

Correlations to other autoantibody species. Overlapping reactivity between DNA and Sm antigens has been reported in several publications (Bloom et al., 1993; Reichlin et al., 1994; Zhang et al., 1995). While in these studies full-length SmD was used, in present invention, there was also a correlation of the anti-dsDNA and anti-S33 reactivity (p<0.0001). Apart from DNA the present invention also shows a positive correlation of anti-S33 to U1-68 (p<0.0001), U1-A (p<0.0001), U1-C (p<0.0001), SmBB' (p<0.0001), Sm (p<0.0001) and SmD (p<0.0001), but not to histones (p=0.0259), La (p=0.8747), Ro-52 (p=0.4034) and Ro-60 (p=0.0143). Whether the observed associations are caused by cross-reactivity or by different autoantibody species that often occur simultaneously, remains unclear. Further studies have to be addressed to shed more light on this issue.

Riemekasten vs Brahms. The obvious conflict between the results of Riemekasten et al. and Brahms et al. might be explained by the existence of different epitopes on the C-terminal extensions of SmD1. The peptide aa 83-119 (Riemekasten et al., 1998) may form a conformational epitope, whereas the shorter peptides used in the second study contain linear, sDMA dependent binding sites (Brahms et al., 2000). Furthermore, the reduced reactivity against the full-length SmD1 (Riemekasten et al., 1998), compared to SmD1$_{83-119}$ peptide, suggests that this peptide epitope represents a cryptic structure. This observation raises the question, which epitopes are "seen" in vivo and which ones play the central role in the pathogenesis of SLE. In a recent study it became evident, that the injection of SmD1$_{83-119}$ fused to a carrier protein is able to accelerate the pathogenic process of Lupus-prone mice (Riemekasten et al., 2001).

"Rhupus"-Syndrom. Rheumatoid Arthritis (RA) and systemic lupus erythremtosus (SLE) are related disorders with an autoimmune etiology. Both diseases are accompanied by the occurrence of self-reactive antibodies to defined structures. Several studies have reported overlap syndromes between RA and Lupus, which were therefore sometimes called the "Rhupus"-Syndrom (Miyachi and Tan, 1979; Panush et al., 1988; Brand et al., 1992). In the presented examples one patient was found within the RA group who demonstrated anti-S33 reactivity (24.6 U/ml). Whether this result reflects a false positive testing or wether autoantibodies to the S33 peptide represent a precursor of lupus-like conditions remains unclear and has to be investigated.

REFERENCES

Abuaf N, Johanet C, Chretien P, Absalon B I, Homberg J C, Buri J F. Detection of autoantibodies to Sm antigen in systemic lupus erythematosus by immunodiffusion, ELISA and immunoblotting: variability of incidence related to assays and ethnic origin of patients. Eur J Clin Invest. August 1990;20(4):354-9.

Arbuckle M R, Reichlin M, Harley J B, James J A. Shared early autoantibody recognition events in the development of anti-Sm B/B' in human lupus. Scand J Immunol. November 1999;50(5):447-55.

Arnett F C, Edworthy S M, Bloch D A, McShane D J, Fries J F, Cooper N S, Healey L A, Kaplan S R, Liang M H, Luthra H S, et al. The American Rheumatism Association 1987 revised criteria for the classification of rheumatoid arritis. Arthritis Rheum. March 1988;31(3):315-24.

Arnett F C, Hamilton R G, Roebber M G, Harley J B, Reichlin M. Increased frequencies of Sm and nRNP autoantibodies in American blacks compared to whites with systemic lupus erythematosus. J Rheumatol December 1988;15(12):1773-6

Bloom D D, Davignon J L, Cohen P L, Eisenberg R A, Clarke S H. Overlap of the anti-Sm and anti-DNA responses of MRL/Mp-lpr/lpr mice. J Immunol. Feb. 15 1993;150(4): 1579-90.

Brahms H, Raker V A, van Venrooij W J, Luhrmann R. A major, novel systemic lupus erythematosus autoantibody class recognizes the E, F, and G Sm snRNP proteins as an E-F-G complex but not in their denatured states. Arthritis Rheum. April 1997;40(4):672-82.

Brahms, H., Raymackers, J., Union, A., de Keyser, F., Meheus, L., Lührmann, R., The C-terminal RG dipeptide repeats of the spliceosomal Sm proteins D1 and D3 contain symmetrical dimethylarginines, which form a major B-cell epitope for anti-Sm autoantibodies. J. Biol. Chem. 275, 17122-17129, 2000.

Brahms H, Meheus L, de Brabandere V, Fischer U, Luhrmann R. Symmetrical dimethylation of arginine residues in spliceosomal Sm protein B/B' and the Sm-like protein LSm4, and their interaction with the SMN protein. RNA. November 2001;7(11):1531-42.

De Keyser F, Hoch S O, Takei M, Dang H, De Keyser H, Rokeach L A, Talal N. Cross-reactivity of the B/B' subunit of the Sm ribonucleoprotein autoantigen with proline-rich polypeptides. Clin Immunol Immunopathol March 1992; 62(3):285-90

Gausepohl, H., Behn, C. Automated Synthesis of Solid-Phase Bound Peptides. In "Peptide Arrays on Membrane supports, Synthesis and Applications" (J. Koch and M. Mahler, Eds), pp. 55-68, Springer Verlag, Heidelberg, N.Y., 2002.

Greidinger E L, Hoffman R W. The appearance of U1 RNP antibody specificities in sequential autoimmune human antisera follows a characteristic order that implicates the U1-70 kd and B'/B proteins as predominant U1 RNP immunogens. Arthritis Rheum. February 2001;44(2):368-75.

Hirakata M, Craft J, Hardin J A. Autoantigenic epitopes of the B and D polypeptides of the U1 snRNP. Analysis of domains recognized by the Y12 monoclonal anti-Sm antibody and by patient sera. J Immunol. Apr. 15, 1993;150(8 Pt 1):3592-601.

Hoch S O, Eisenberg R A, Sharp G C. Diverse antibody recognition patterns of the multiple Sm-D antigen polypeptides. Clin Immunol. August 1999;92(2):203-8.

Hoch, S. O., The Sm antigens. In "Manual of biological Markers of disease" (R. N. Maini and W. J. van Venrooji, Eds.), pp. B2.4/1-29, Kluwer Academic, Dordrecht, The Netherlands, 1994.

Jaekel H P, Klopsch T, Benkenstein B, Grobe N, Baldauf A, Schoessler W, Werle E. Reactivities to the Sm Autoantigenic Complex and the Synthetic SmD1-aa83-119 Peptide in Systemic Lupus Erythematosus and other Autoimmune Diseases. J Autoimmun. December 2001;17(4):347-54.

James J A, Kaufman K M, Farris A D, Taylor-Albert E, Lehman T J, Harley J B. An increased prevalence of Epstein-Barr virus infection in young patients suggests a possible etiology for systemic lupus erythematosus. J Clin Invest. Dec. 15, 1997;100(12):3019-26.

Lehmeier T, Raker V, Hermann H, Luhrmann R. CDNA cloning of the Sm proteins D2 and D3 from human small nuclear ribonucleoproteins: Evidence for a direct D1-D2 interaction. Proc. Natl. Acad. Sci. December 1994;91: 12317-12321

Lerner M R, Boyle J A, Mount S M, Wolin S L, Steitz J A. Are snRNPs involved in splicing? Nature. Jan. 10, 1980;283 (5743):220-4.

Mahler M, Mierau R, Schlumberger W, Bluthner M. A population of autoantibodies against a centromere-associated protein A major epitope motif cross-reacts with related cryptic epitopes on other nuclear autoantigens and on the Epstein-Barr nuclear antigen 1. J Mol Med 79, 722-31

Marchini B, Dolcher M P, Sabbatini A, Klein G, Migliorini P. Immune response to different sequences of the EBNA I molecule in Epstein-Barr virus-related disorders and in autoimmune diseases. J Autoimmun. April 1994;7(2):179-91.

McClain M T, Ramsland P A, Kaufman K M, James J A. Anti-sm autoantibodies in systemic lupus target highly basic surface structures of complexed spliceosomal autoantigens. J Immunol. Feb. 15, 2002;168(4):2054-62.

Panush R S, Edwards N L, Longley S, Webster E. 'Rhupus' syndrome. Arch Intern Med. July 1988;148(7):1633-6.

Reichlin M, Martin A, Taylor-Albert E, Tsuzaka K, Zhang W, Reichlin M W, Koren E, Ebling F M, Tsao B, Hahn B H. Lupus autoantibodies to native DNA cross-react with the A and D SnRNP polypeptides. J Clin Invest. January 1994; 93(1):443-9.

Riemekasten G, Marell J, Trebeljahr G, Klein R, Hausdorf G, Haupl T, Schneider-Mergener J, Burmester G R, Hiepe F. A novel epitope on the C-terminus of SmD1 is recognized by the majority of sera from patients with systemic lupus erythematosus. J Clin Invest. Aug. 15, 1998;102(4):754-63.

Riemekasten G, Kawald A, Weiss C, Meine A, Marell J, Klein R, Hocher B, Meisel C, Hausdorf G, Manz R, Kamradt T, Burmester G R, Hiepe F. Strong acceleration of murine lupus by injection of the SmD1(83-119) peptide. Arthritis Rheum. October 2001;44(10):2435-45.

Roeach L A, Haselby J A, Hoch S O. Molecular cloning of a cDNA encoding the human Sm-D autoantigen. Proc. Natl. Acad. Sci July 1988; 85(13): 4832-6

Rokeach L A, Jannatipour M, Haselby J A, Hoch S O. Mapping of the immunoreactive domains of a small nuclear ribonucleoprotein-associated Sm-D autoantigen. Clin Immunol Immunopathol. December 1992;65(3):315-24.

Rokeach L A, Hoch S O. B-cell epitopes of Sm autoantigens. Mol Biol Rep. June 1992;16(3):165-74. Review.

Sabbatini A, Bombardieri S, Migliorini P. Autoantibodies from patients with systemic lupus erythematosus bind a shared sequence of SmD and Epstein-Barr virus-encoded nuclear antigen EBNA I. Eur J Immunol May 1993;23(5): 1146-52

Sabbatini A, Dolcher M P, Marchini B, Bombardieri S, Migliorini P. Mapping of epitopes on the SmD molecule: the use of multiple antigen peptides to measure autoantibodies in systemic lupus erythematosus. J Rheumatol. October 1993;20(10):1679-83.

Seraphin B. Sm and Sm-like proteins belong to a large family: identification of proteins of the U6 as well as the U1, U2, U4 and U5 snRNPs. EMBO J. May 1, 1995;14(9):2089-98.

Tan E M, Kunkel H G. Characteristics of a soluble nuclear antigen precipitating with sera of patients with systemic lupus erythematosus. J Immunol. March 1966;96(3):464-71.

Tan E M, Cohen A S, Fries J F, Masi A T, McShane D J, Rothfield N F, Schaller J G, Talal N, Winchester R J. The 1982 revised criteria for the classification of systemic lupus erythematosus. Arthritis Rheum. November 1982;25(11): 1271-7.

von Muhlen C A, Tan E M. Autoantibodies in the diagnosis of systemic rheumatic diseases. Semin Arthritis Rheum. April 1995;24(5):323-58. Review.

Ou Y, Sun D, Sharp G C, Hoch S O. Screening of SLE sera using purified recombinant Sm-D1 protein from a baculovirus expression system. Clin Immunol Immunopathol. June 1997;83(3):310-7.

Zhang W, Reichlin M. IgM anti-A and D SnRNP proteins and IgM anti-dsDNA are closely associated in SLE sera. Clin Immunol Immnunopathol. January 1995;74(1):70-6.

Preliminary criteria for the classification of systemic sclerosis (scleroderma). Subcommittee for scleroderma criteria of the American Rheumatism Association Diagnostic and Therapeutic Criteria Committee. Arthritis Rheum. May 1980;23(5):581-90.

The invention claimed is:

1. A peptide consisting of the amino acid sequence AARGsdRGRGMGRGNIF (SEQ ID NO: 1) wherein the amino acid sdR is symmetric dimethylated arginine having the structure

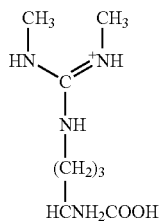

and wherein the peptide is able to react with antibodies which are presented in sera from patients with systemic lupus erythematosus (SLE).

2. A method of diagnosing systemic lupus erythematosus (SLE), comprising contacting sera of a patient with a composition comprising the peptide of claim 1.

3. The method according to claim 2, wherein the diagnosis is differential diagnosis to distinguish between SLE patients and patients with mixed connective tissue disease (MCTD).

4. The method according to claim 2, wherein the diagnosis is an in vitro diagnosis of SLE.

5. The method according to claim 2, wherein said composition is used for differentiation between SLE and mixed connective tissue disease (MCTD).

6. A peptide comprising multimers of the peptide of claim 1.

7. A kit for detection of antibodies, comprising the peptide of Claim 1.

8. A kit according to claim 7, wherein said peptide is used for in vitro diagnosis of SLE.

9. A kit according to claim 7, wherein said peptide is used for differential diagnosis to distinguish between SLE and mixed connective tissue disease (MCTD).

10. A method for monitoring a disease activity comprising repeated testing to follow the titer of antibodies able to react with the peptide according to claim 1 in order to monitor the effect of treatment or the disease activity, wherein the disease is SLE.

11. The method according to claim 10, wherein said disease is dsDNA negative SLE.

* * * * *